(12) United States Patent
Cipoletti et al.

(10) Patent No.: US 7,713,245 B2
(45) Date of Patent: May 11, 2010

(54) PLUNGER FOR RETRACTING NEEDLE SYRINGE

(75) Inventors: Robert K. Cipoletti, Pompton Plains, NJ (US); Richard Giddes, Edison, NJ (US); Kanar W. Rabah, Clifton, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1138 days.

(21) Appl. No.: 11/261,271

(22) Filed: Oct. 28, 2005

(65) Prior Publication Data

US 2007/0100293 A1    May 3, 2007

(51) Int. Cl.
*A61M 5/315* (2006.01)
(52) U.S. Cl. ...................................... 604/218
(58) Field of Classification Search .............. 604/181, 604/187, 218–232, 110
See application file for complete search history.

(56) References Cited

U.S. PATENT DOCUMENTS

| | | | | |
|---|---|---|---|---|
| 5,279,606 A | * | 1/1994 | Haber et al. | 604/403 |
| 5,935,104 A | * | 8/1999 | Janek et al. | 604/110 |
| 6,432,087 B1 | * | 8/2002 | Hoeck et al. | 604/181 |
| 2006/0084914 A1 | * | 4/2006 | Tung | 604/110 |

* cited by examiner

*Primary Examiner*—Matthew F Desanto
(74) *Attorney, Agent, or Firm*—Diehl Servilla LLC

(57) ABSTRACT

A plunger for a retracting needle syringe includes a hollow elongate body portion having a proximal end, a distal end, and a side wall therebetween defining a cavity. The distal end includes a distal wall having an inside surface and an outside surface. A stopper, at the distal end of the body portion, includes a peripheral portion performing a seal with the inside surface of a syringe barrel and at least one radial element extending from about a center of the outside surface of the distal wall to the peripheral portion. The distal end of the body portion includes at least one primary chamfer in the cavity at an intersection of the inside surface of the distal wall and the side wall. The chamfer is positioned under the at least one radial element for supporting the distal wall and the radial element when a hollow sleeve in the syringe barrel cuts through the end wall plunger. A secondary, smaller chamfer on each side of the primary chamfer is also provided.

25 Claims, 14 Drawing Sheets

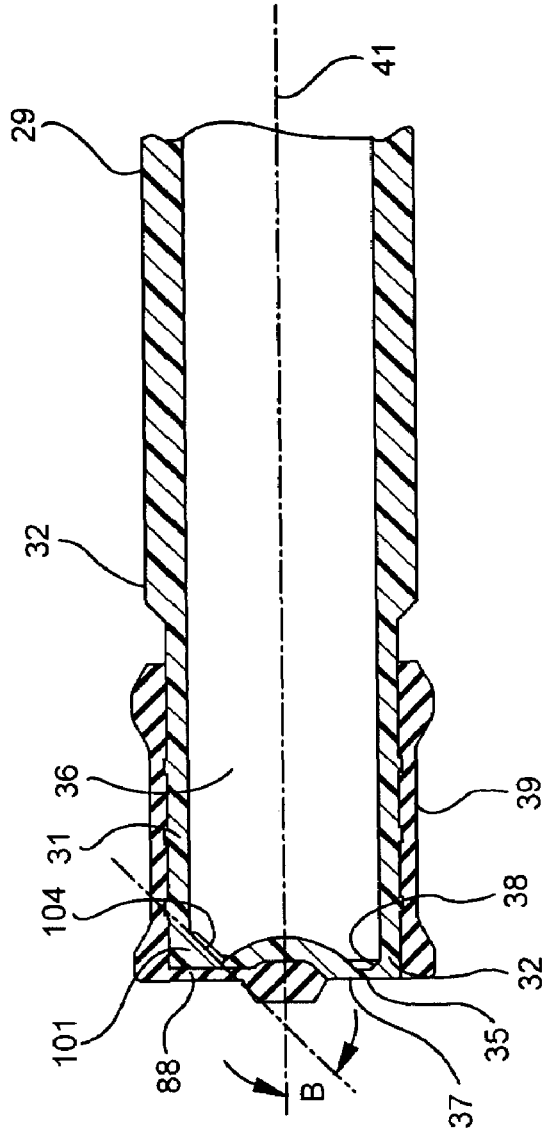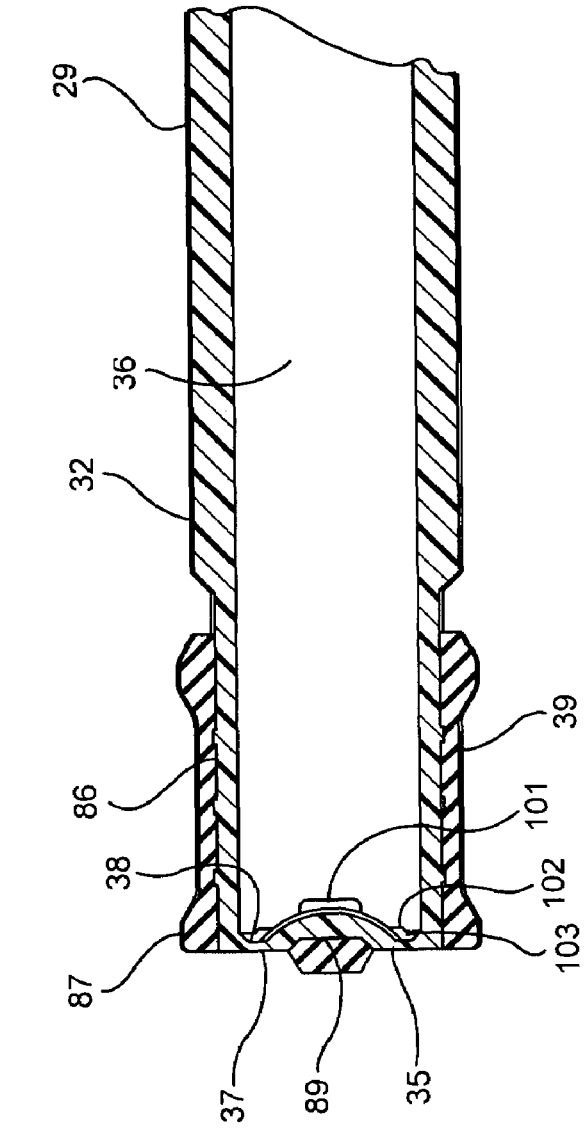
FIG. 7
FIG. 8

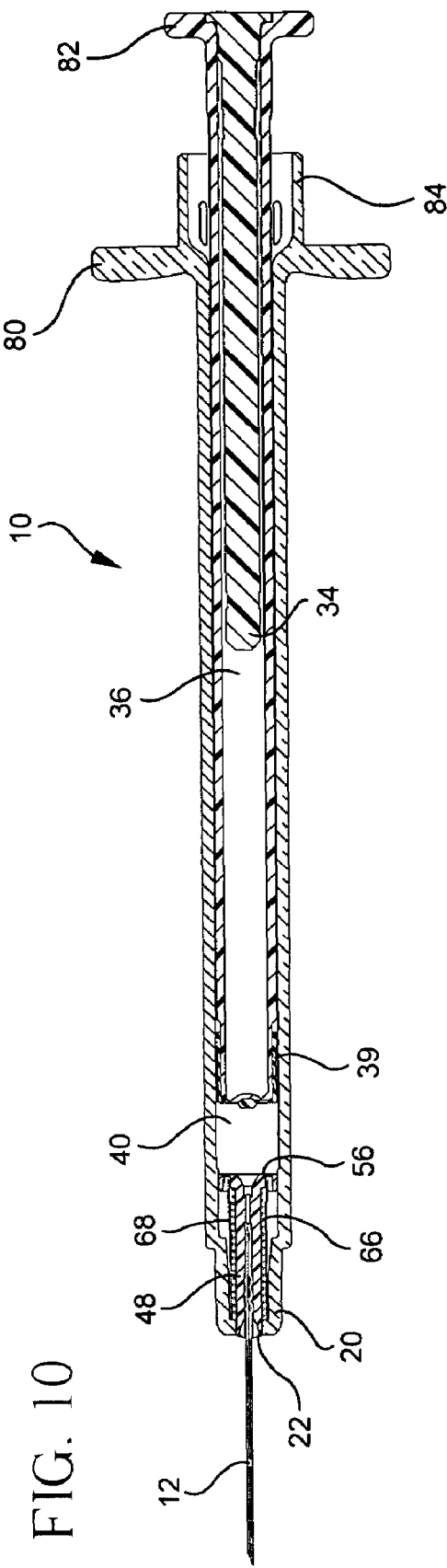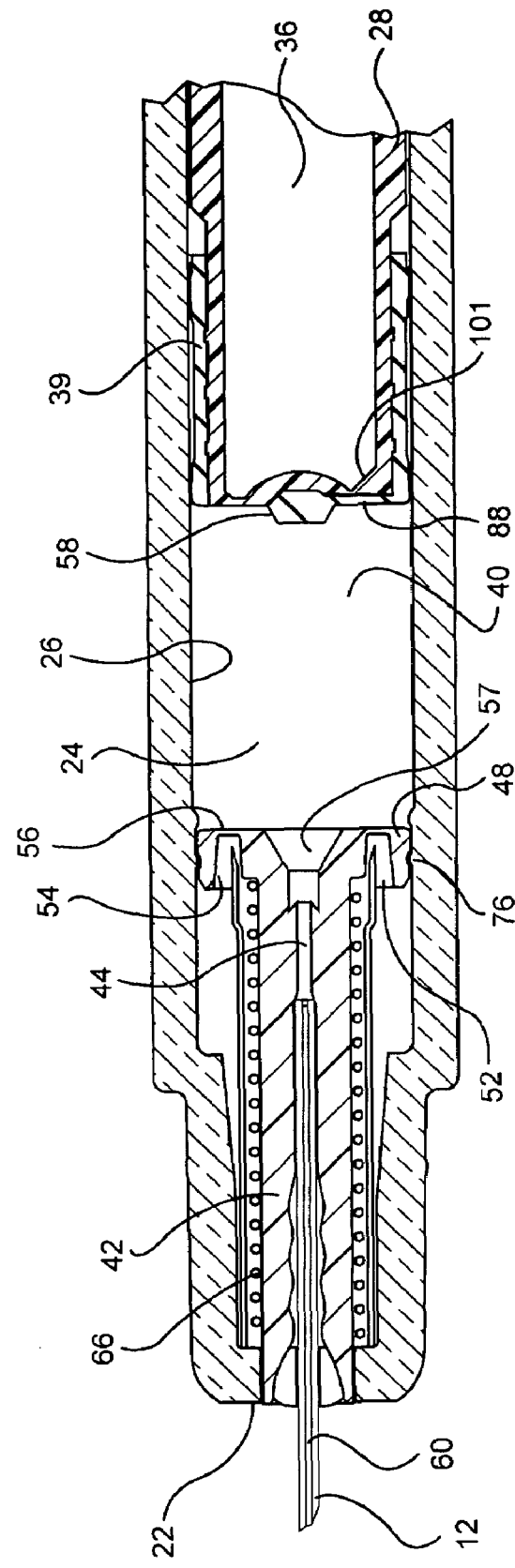
FIG. 10
FIG. 10A

PLUNGER FOR RETRACTING NEEDLE SYRINGE

FIELD OF THE INVENTION

The present invention is generally related to syringes that include a needle that is retractable after the intended use to substantially prevent inadvertent exposure to the needle and reuse of the syringe, and more particularly to an improved plunger for enhancing the needle withdrawal function.

BACKGROUND

Hypodermic syringes are widely used in the medical field for administering medicaments and for drawing body fluid samples. Generally, hypodermic syringes include a needle having a sharpened distal point for penetrating vial stoppers or patient's skin. The needle is attached either fixedly or removably to a syringe barrel. Hypodermic syringes and needles have been used for many years with few problems reported when the vast numbers and needles being used are considered. More recently, with the recognition of viral diseases that are transmitted by body fluids and greater sensitivity of the need to protect health care workers from inadvertent contact with previously used needles (commonly referred to as "sharps") as well as the need to reduce criminal misuse of improperly disposed of needle and syringes, syringes and needles that include provisions to prevent reuse have been developed.

Devices intended to prevent reuse of needles and syringes include a variety of sharps collector systems that are widely used in health care facilities. Other developments include needle attachments that may be readily broken off by practitioners once the syringe has completed its intended use. A variety of shielding mechanisms has been developed; some of which are currently commercially available. While many of these developments have reduced the incidence of inadvertent exposure of healthcare workers to sharps, many of these devices can be overcome by an individual determined to obtain and misuse a hypodermic syringe and needle. As a result of this problem, further developments in the art of hypodermic syringes have resulted in syringes with needles that withdraw into the body of the syringe once their intended use is completed.

Current conventional syringes are considered by users to be virtually fault-free and reliable. They are used for a variety of different procedures involving both "one-shot" fill and inject procedures, as well as more complex mixing, measuring and delivery functions. In order for a retracting needle syringe to replace these functional, utilitarian and reliable conventional syringes, the retracting needle syringe should not significantly interfere with the users' current practices, it needs to be substantially reliable and its cost should not be prohibitive. Current conventional syringes are often manufactured at rates of several hundred per minute and their cost is generally not a significant factor in their usage. Additionally every year, hundreds of millions of small capacity (one milliliter) syringes are used outside of the normal controlled health care environment by diabetics and other self-injectors who must daily accurately inject small amounts of medication or other liquid, often only a few tenths of a milliliter. These small capacity syringes are usually physically small, with an overall length of less than five inches and an inside bore diameter of about one-quarter inch. In light of the discussions above, one skilled in the art of high volume manufacturing recognizes that assembling hundreds of millions of most of these relatively complex devices with their retraction elements contained in such a small space as a one-quarter inch diameter bore is a difficult task.

The need thus exists for a selectively retracting needle syringe that is compatible with a small capacity syringe without retracting needle features, that is capable of being manufactured at high volumes and is sufficiently non-complex to be reliable in use when produced at volumes of hundreds of millions per year. Such a device is disclosed in U.S. Pat. Nos. 6,432,087; 6,679,863 and 6,689,106. The invention disclosed herein represents an improvement of the plunger and stopper of the syringes described in the aforementioned U.S. patents and any other design of single-use syringe using a barrel or needle assembly based cutting element intended to cut through the stopper and the plunger from the distal end of the plunger rod assembly.

SUMMARY OF THE INVENTION

The present invention relates to a plunger for an operable retracting needle syringe. The operable retracting needle syringe includes a barrel having an inside surface defining a chamber, an open proximal end, a distal end including a needle assembly having a hub connected to the distal end of the barrel and a needle having a sharp distal end. The proximal end of the needle is connected to the hub and a lumen in the needle is in fluid communication with the chamber in the barrel. The hub further includes a biasing spring operatively connected to a hollow cutting sleeve having a proximally facing sharp edge capable of cutting through the hub and the plunger. The plunger of the present invention comprises a hollow elongate body portion having a proximal end, a closed distal end and a side wall therebetween defining a cavity therein and including a longitudinal axis. The distal end of the plunger includes a distal wall having an inside surface and an outside surface. A stopper at the distal end of the plunger includes a peripheral portion having an outside surface for forming a seal on the inside surface of the barrel. The stopper has at least one radial element extending from about a center of the outside surface of the distal wall of the plunger body portion to the peripheral portion. The distal end of the plunger body portion includes at least one primary chamfer in the cavity at the intersection of the inside surface of the distal wall and the side wall. The primary chamfer is positioned under the at least one radial element of the stopper for supporting the distal wall and the at least one radial element when the hollow sleeve cuts through the end wall. A secondary chamfer on each side of the at least one primary chamfer is provided. Each secondary chamfer is smaller than the primary chamfer.

An alternative embodiment of the plunger of the present invention includes a stopper having two radial elements and two primary chamfers positioned and under the radial elements. In this embodiment it is preferred that the two radial elements radiate in substantially opposite directions. The plunger of the present invention desirably includes a tertiary chamfer adjacent to each secondary chamfer wherein the tertiary chamfers are smaller than the secondary chamfers. Although the chamfers are preferably distinct elements, an alternative may include the primary and secondary chamfers being blended together in a relatively smooth transition and/or the secondary chamfers and the tertiary chamfers can be blended together in a relatively smooth transition.

The body portion of the plunger is preferably made of thermoplastic material and the stopper is preferably made of a thermoplastic elastomer. The elongate body portion and the stopper are preferably molded in a two-step molding process to form an integral plunger.

It is preferred that the primary chamfer extend for about the same number of degrees along the intersection of the inside surface of the distal wall of the plunger and the side wall of the plunger as a width of said radial element of the stopper adjacent to the primary chamfer, as measured from the plunger longitudinal axis. The preferred chamfer has an angle of between 40 and 50° measured from the longitudinal axis. The secondary chamfer also desirably is formed at an angle of 40 to 50° as measured from the longitudinal axis and is preferably no more than about 60 percent as high as the primary chamfer measured along the longitudinal axis. The shape of the primary chamfer face as viewed through a cross-sectional view is a straight line or planar, however, convex and concave shapes and combinations thereof are within the purview of the present invention.

The plunger preferably includes a centrally-located distally-directed projection for entering a recess in the proximal end of the hub for reducing the amount of liquid in the barrel after injection. The distally-directed projection is preferably frusto-conically shaped.

In an embodiment of the present invention wherein the operable retracting needle syringe is capable of delivering a dose of about 1 ml the body portion of the plunger has an inside diameter at its distal end of 2.9 to 3.4 mm (0.115 to 0.135 inch). The primary chamfer is between 0.38 mm (0.015 inch) and 0.64 mm (0.025 inch) high.

BRIEF DESCRIPTION OF THE DRAWINGS

FIG. 7 is a cross-sectional side elevation view of the plunger of FIG. 5 taken along line 7-7.

FIG. 8 is a cross-sectional side elevation view of the plunger of FIG. 5 taken along line 8-8.

FIG. 10 is a cross-sectional view of the syringe of FIG. 1 with the plunger partially distally retracted taken on the line 10-10;

FIG. 10A is an enlargement of a distal portion of the cross-sectional view of FIG. 10;

DETAILED DESCRIPTION

Figure 1:
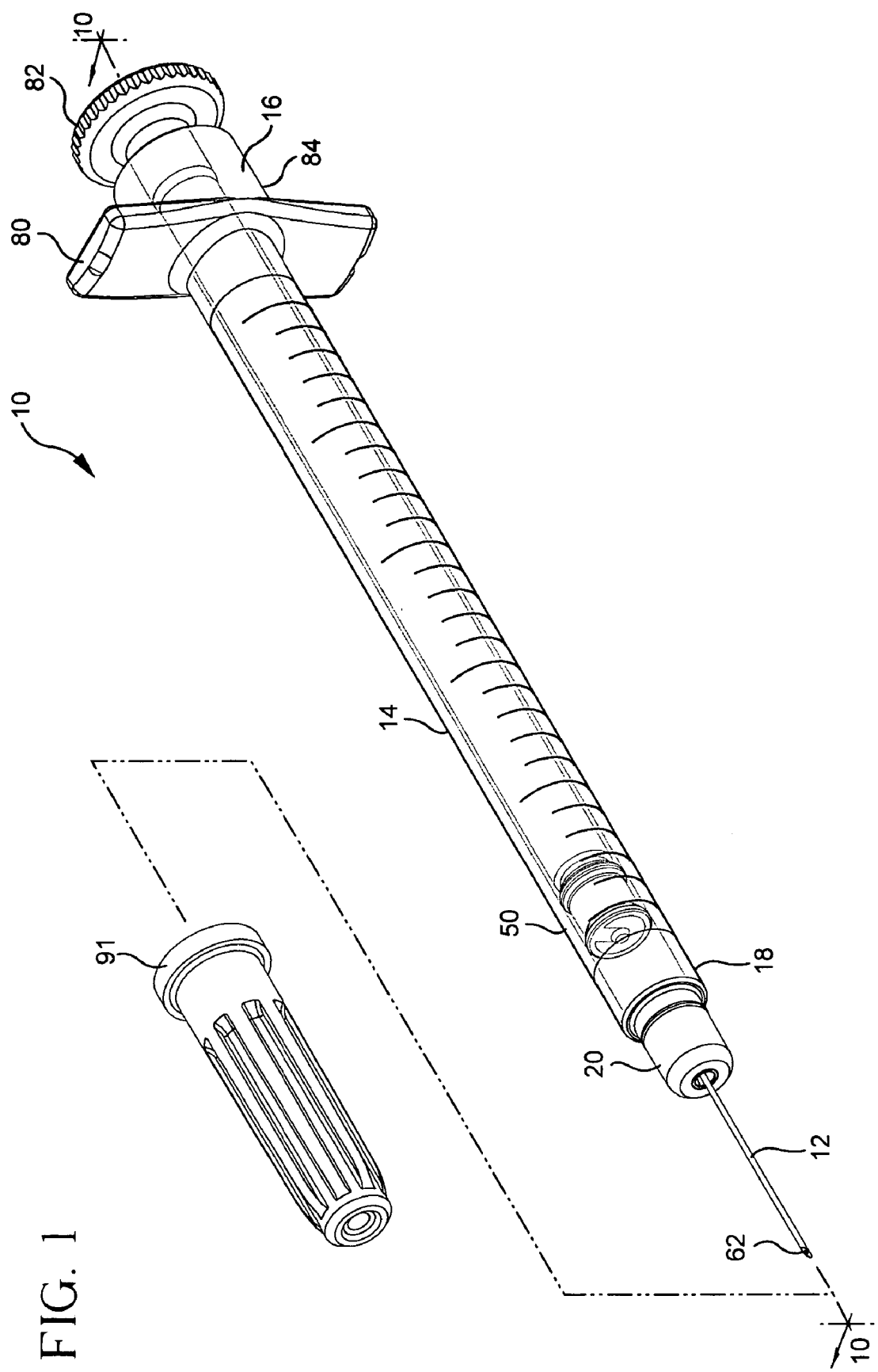
FIG. 1 is a partially exploded perspective view of one embodiment of a hypodermic syringe having a retractable needle in accordance with the present invention.
Figure 2:
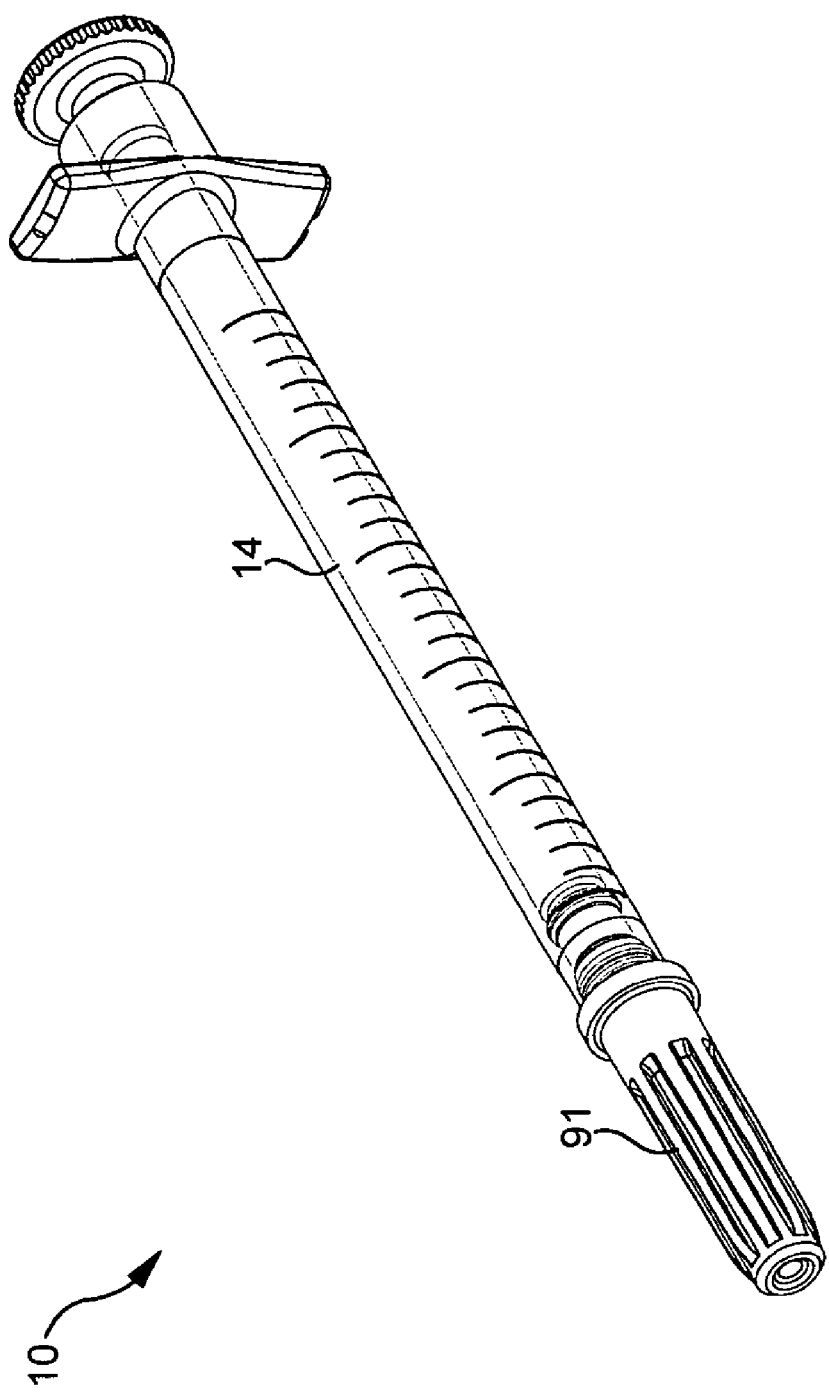
FIG. 2 is a perspective view of the hypodermic syringe of FIG. 1 assembled.
Figure 3:
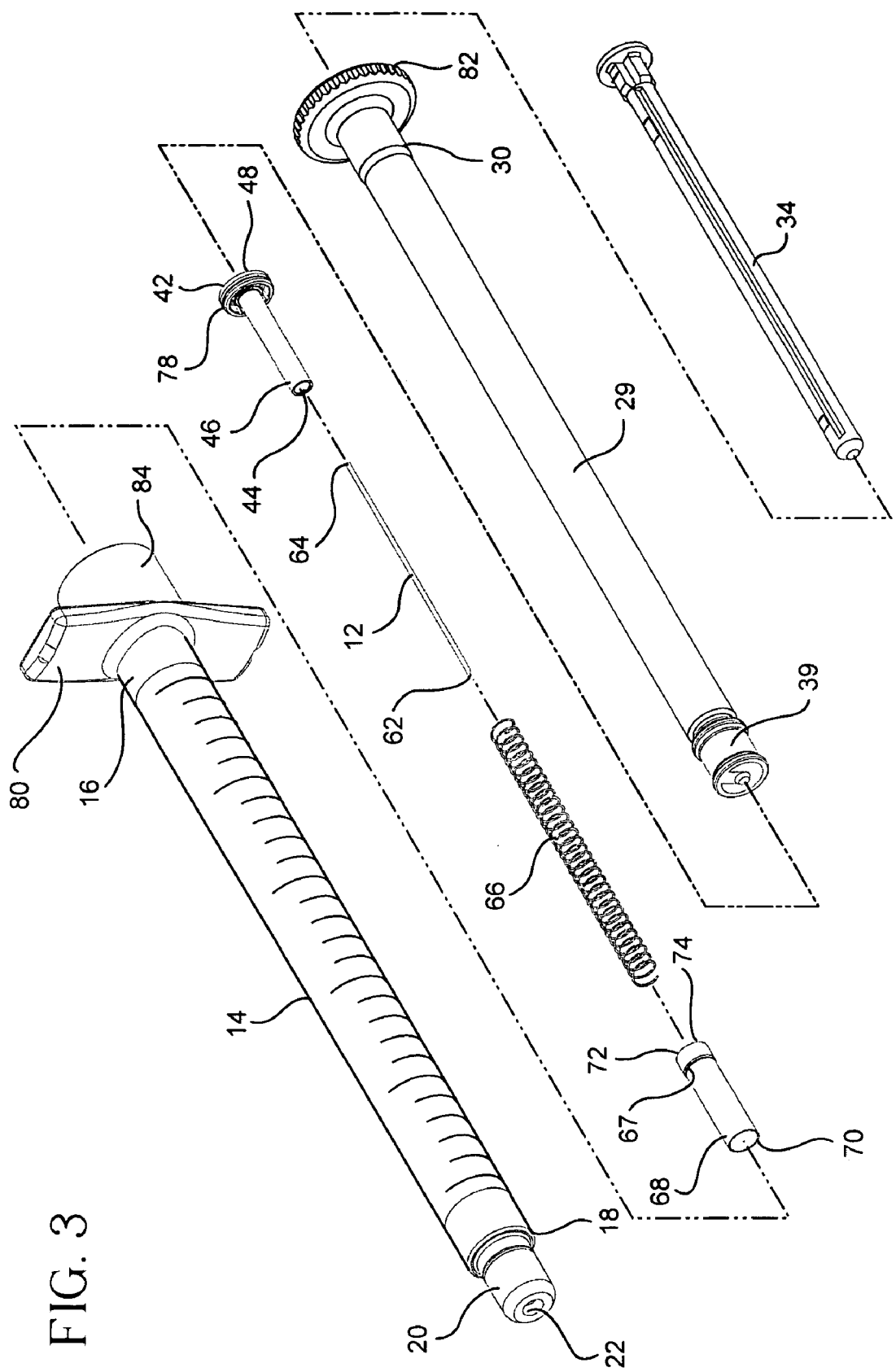
FIG. 3 is an exploded perspective view of the hypodermic syringe of FIG. 1.
Figure 4:
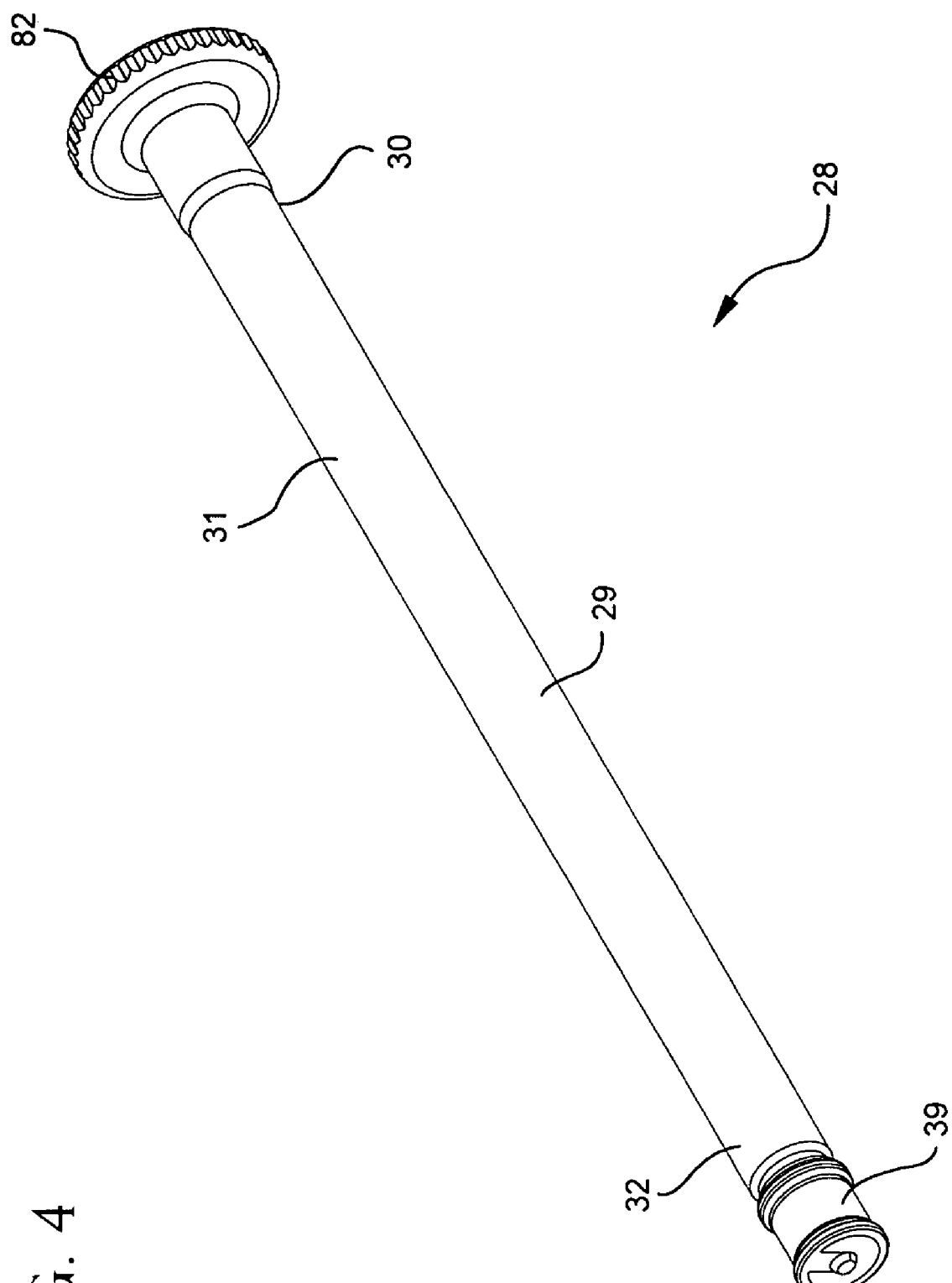
FIG. 4 is a perspective view of an embodiment of the plunger of the present invention.
Figure 5:
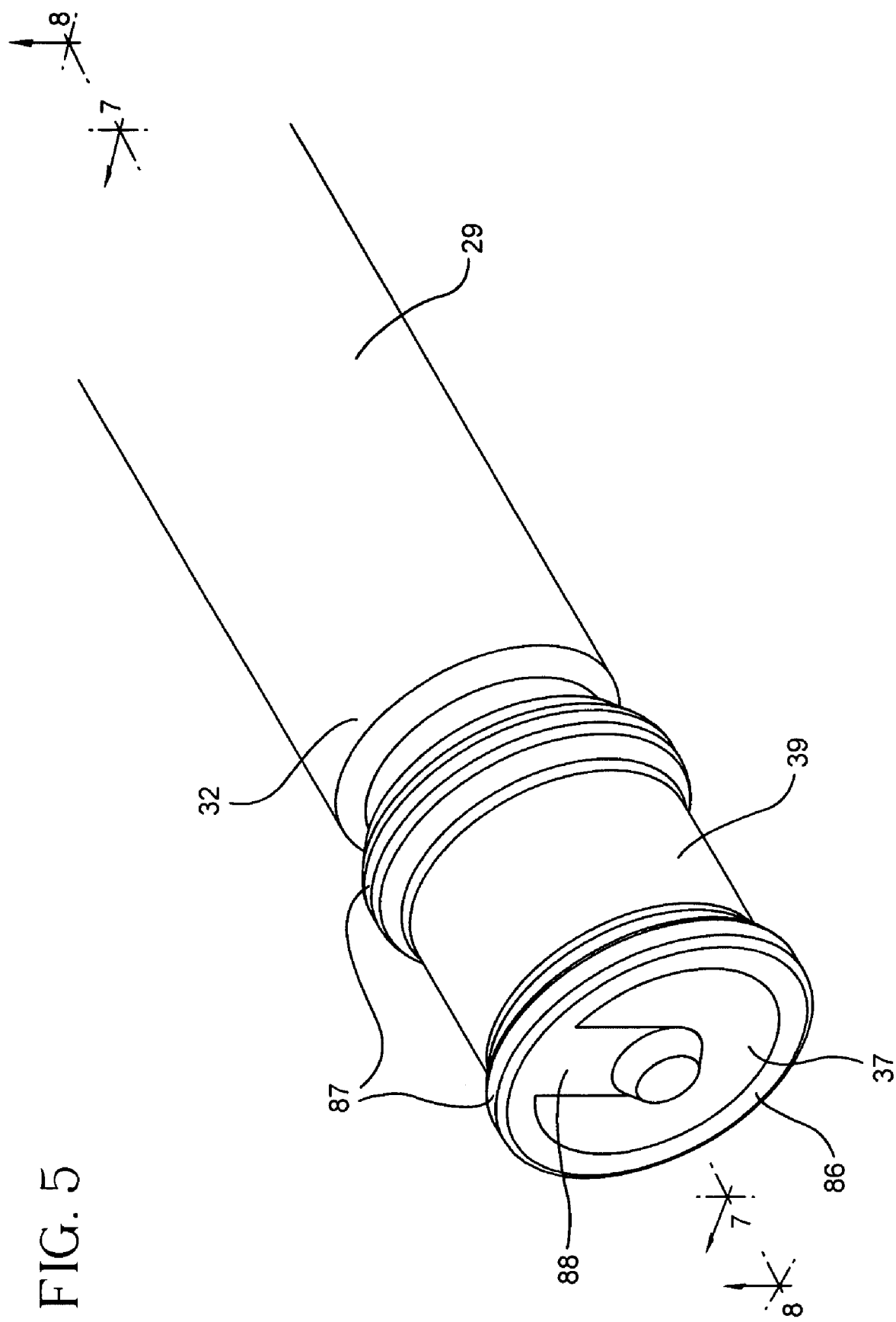
FIG. 5 is an enlarged perspective view of the distal end of the plunger of FIG. 4.
Figure 6:
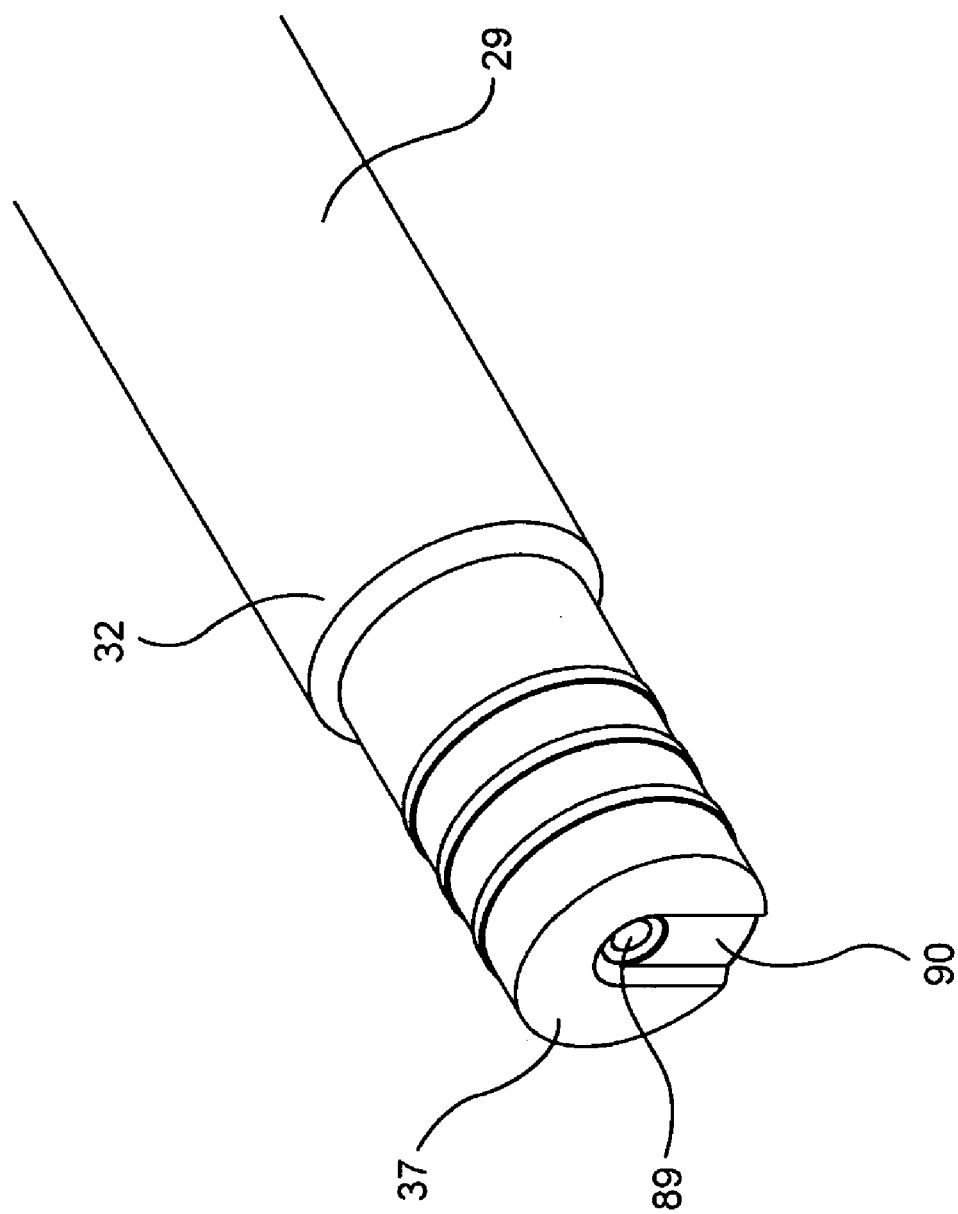
FIG. 6 is an enlarged perspective view of the distal end of the plunger of FIG. 4, before the stopper is molded onto the distal end of the body portion of the plunger.

While this invention is satisfied by embodiments in many different forms, there are shown in the drawings and herein described in detail, embodiments of the invention with the understanding that the present disclosure to be considered as exemplary of the principles of the present invention and is not intended to limit the scope of the invention to the embodiments illustrated. The scope of the invention is measured by the appended claims and the equivalents. In this disclosure, a convention is followed wherein the distal end of the device is the end closest to a patient and the proximal end of the device is the end away from the patient and closest to a practitioner.

Figure 12:
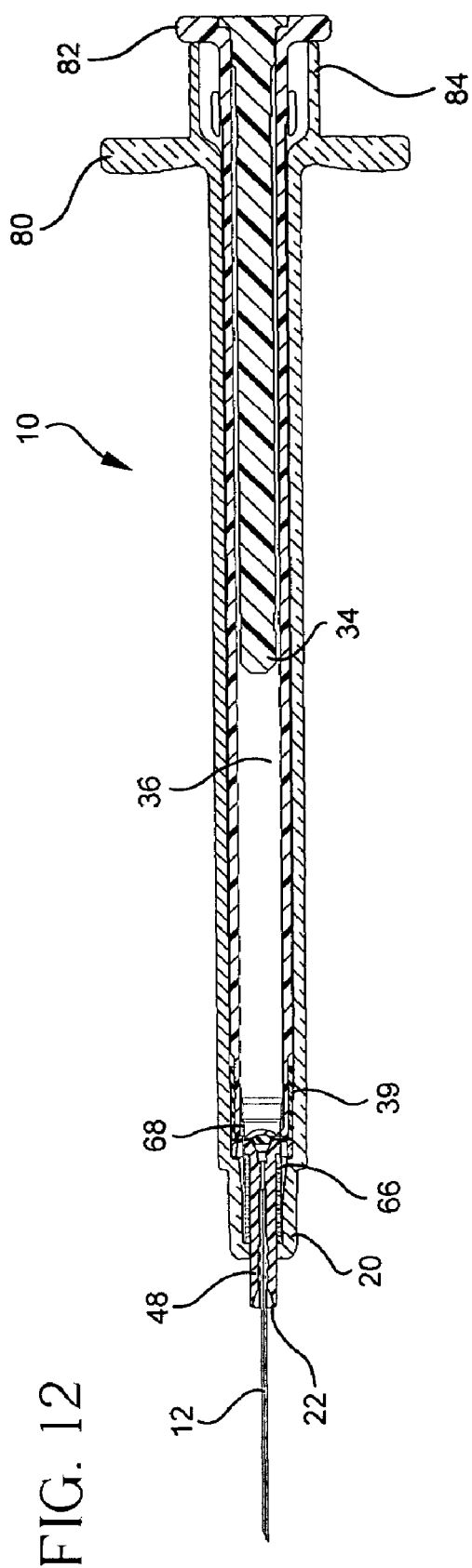
FIG. 12 is a cross-sectional view of the syringe of FIG. 1 with the plunger moved distally to activate the needle retraction sequence.
Figure 12A:
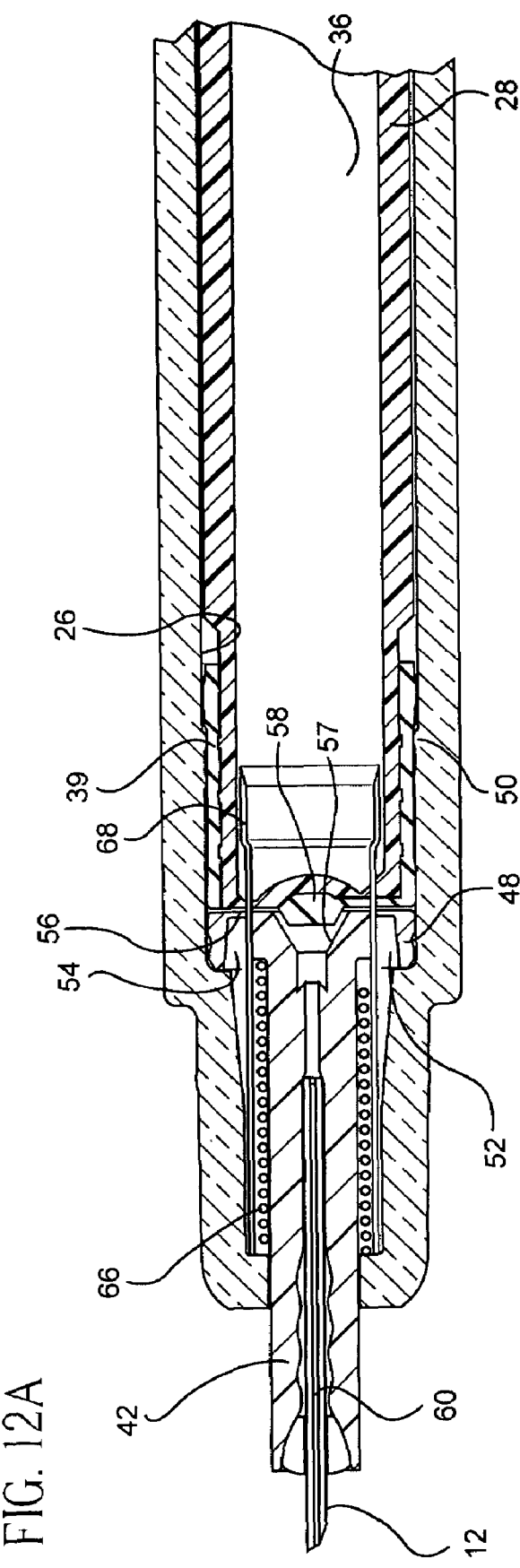
FIG. 12A is an enlargement of the distal portion of the cross-sectional view of FIG. 12.
Figure 13:
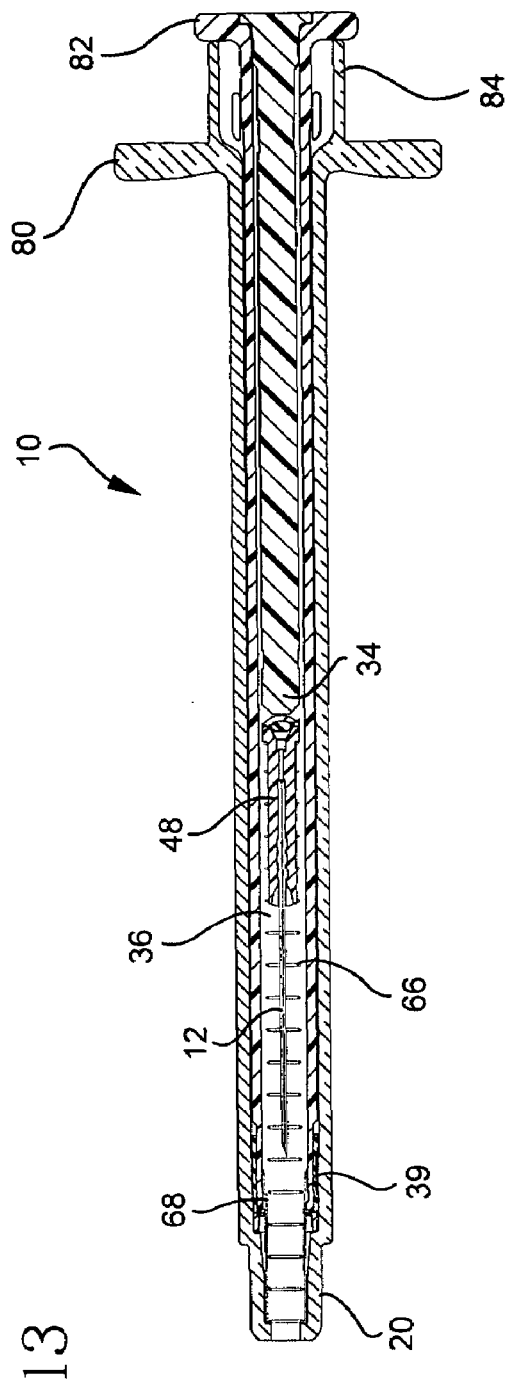
FIG. 13 is a cross-sectional view of the syringe of FIG. 1 shown after the needle retraction sequence is completed.
Figure 13A:
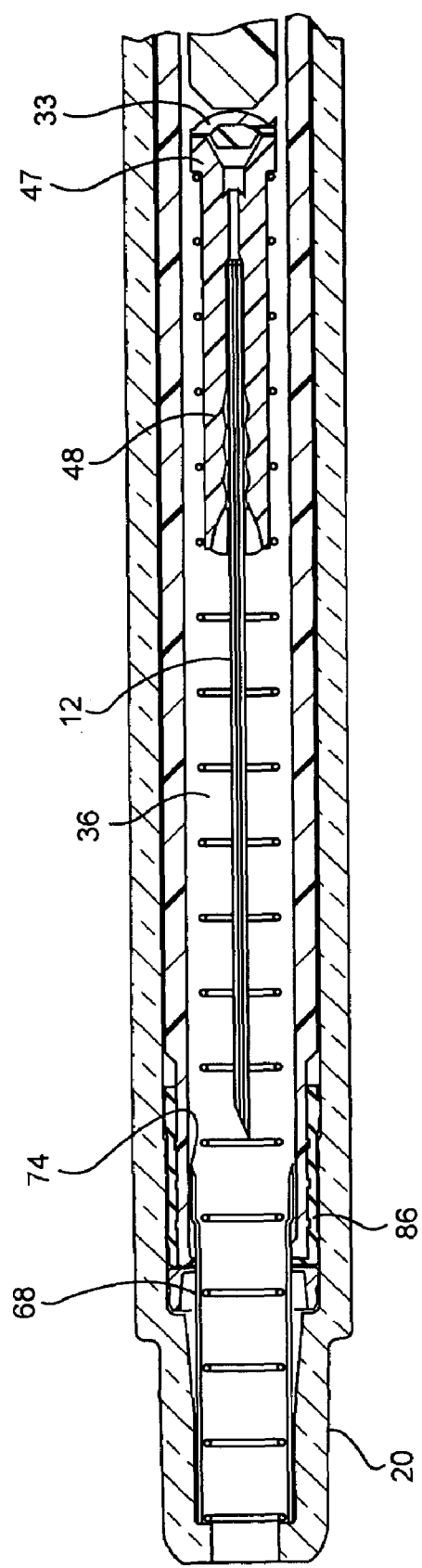
FIG. 13A is an enlargement of a portion of the cross-sectional view of FIG. 13.

Referring to the FIGS. 1-13A, a syringe assembly 10 with a selectively retractable needle 12 in accordance with an embodiment of the present invention includes an elongate barrel 14 having an open proximal end 16 and a distal end 18 that defines a receiver 20 with an inwardly projecting shoulder 22. Barrel 14 has a hollow bore 24 therethrough with an inside surface 26. Syringe 10 includes a plunger 28 having a hollow elongate body portion 29 with an open proximal end 30 and a closed distal end 32. There is an elongate plug 34 extending distally into hollow body portion 29 from open proximal end 30. A stopper 39 at distal end 32 of plunger 28 forms a slidable seal with inside surface 26 of the barrel to define a chamber 40 for drawing and expelling fluid. Syringe 10 also includes an elongate hub 42 having a passageway 44 therethrough, a distally extending stem 46, a proximal flange 48 with an engagement structure 50 for engaging the barrel. Stem 46 is disposed within and sized for slidable movement within receiver 20 at distal end 18 of the barrel. Flange 48 has a distal surface 52 having a groove 54 therein and a proximal surface 56 facing a chamber 40 in the barrel. Proximal surface 56 desirably includes a frusto-conically shaped recess 57. Elongate needle 12 includes a lumen 60 therethrough a sharp distal end 62 and a proximal end 64. Needle 12 is mounted in passageway 44 in hub 42 so that sharp distal end 62 projects distally outwardly and lumen 60 is in fluid communication with chamber 40 in the barrel. An elongate spring 66 disposed about stem 46 of hub 42 is compressed between flange 48 and inwardly projecting shoulder 22 of receiver 20 to provide a bias. There is a hollow sleeve 68 sized to fit within receiver 20 over elongate spring 66. Sleeve 68 has a distal end 70 disposed at shoulder 22 and a proximal end 72 with a sharp cutting edge 74 that is disposed in groove 54 in distal surface 52 of the flange. When a user applies a sufficient force as illustrated in FIGS. 12 and 12A, a force greater than necessary to expel fluid from chamber 40, to plunger 28, hub 42 is sufficiently moved distally in receiver 20 for cutting edge 74 of sleeve 68 to cut through flange 48 and closed distal end 32 of the plunger including portions of stopper 39 to expose cavity 36 in the plunger. When cavity 36 in the plunger is exposed, the bias of spring 66 urges a sufficient movement of a cut portion 47 of the hub having needle 12 mounted therein, a cut portion 33 of distal end 32 of the plunger including portions of stopper 39 and sleeve 68 into cavity 36 in the plunger to a position, best seen in FIGS. 13 and 13A, wherein an inadvertent exposure of sharp distal point 62 is substantially prevented.

In particular, as shown in FIGS. 3-9, closed distal end 32 of elongate body portion 29 and proximal end 30 have a side wall 31 therebetween defining cavity 36 therein and including a longitudinal axis 41. Distal end 32 includes distal wall 35 having an outside surface 37 and an inside surface 38.

Figure 11:
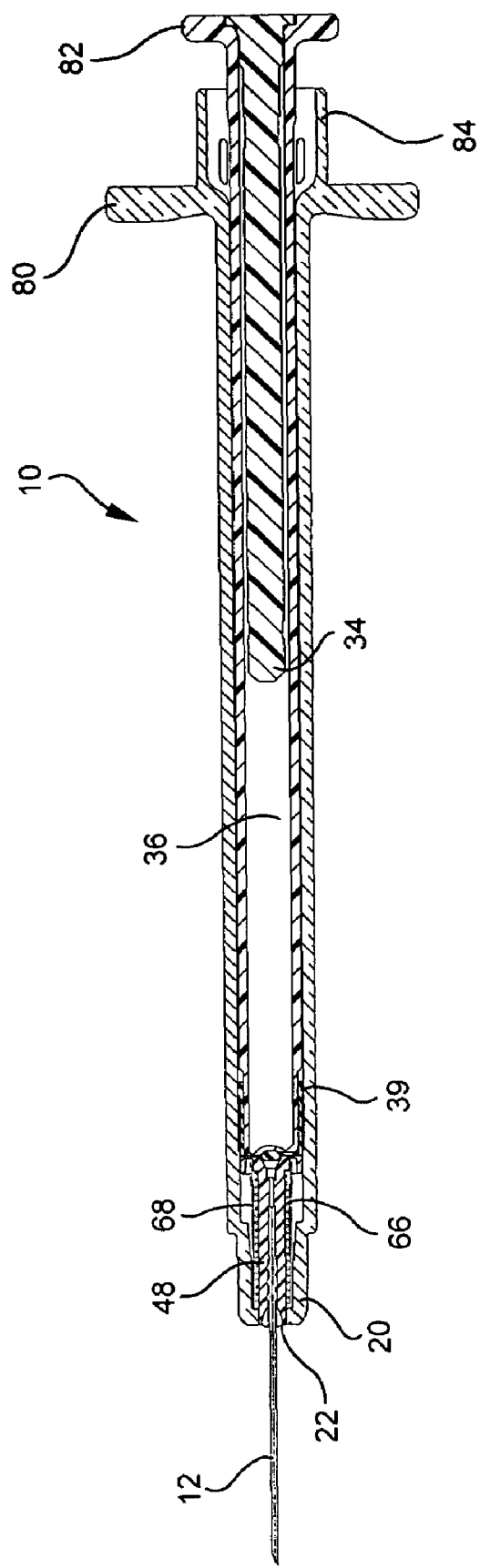
FIG. 11 is a cross-sectional view of the syringe of FIG. 1 with the plunger at the distal end of the barrel.
Figure 11A:
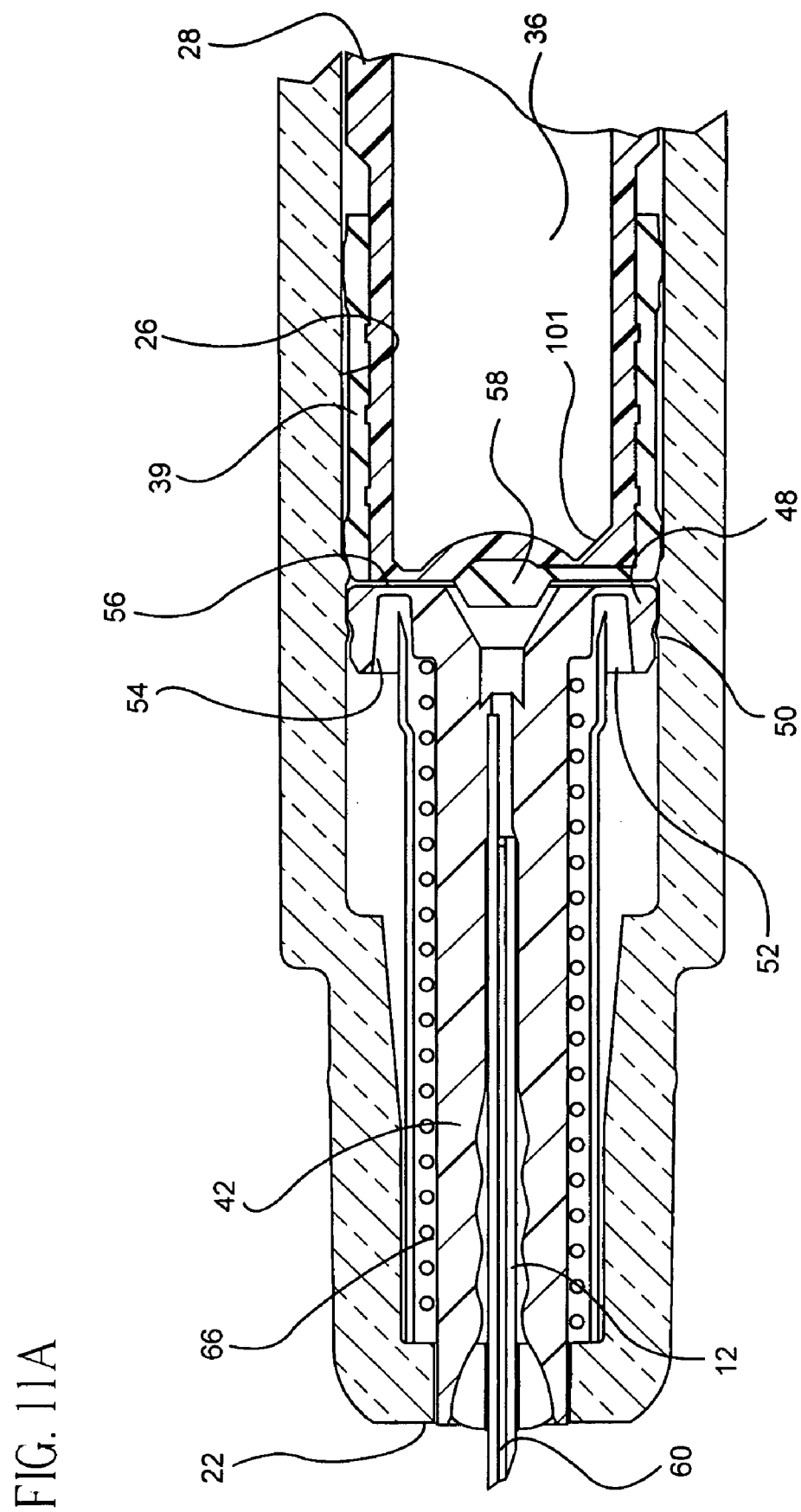
FIG. 11A is an enlargement of the distal portion of the cross-sectional view of FIG. 11.

Stopper 39 at distal end 32 of the elongate body portion 29 includes a peripheral portion 86 forming a seal with the inside surface of the barrel. The stopper includes at least one radial element 88 extending from about a center 89 of outside surface 37 of the distal wall to peripheral portion 86. Stopper 39 preferably includes a centrally located distally directed projection 58 sized and shaped to fit into recess 57 of the hub. In this embodiment the distally directed projection is preferably frusto-conically shaped. Projection 58, as shown in FIGS. 10A and 11A, helps to minimize dead space containing liquid, such as medication, that cannot be delivered through the needle. Accordingly, this feature reduces lost medication remaining in the barrel after injection and can result in substantial savings especially in mass injection programs where hundreds or thousands of people are being injected.

Elongate body portion 29 is preferably formed by an injection molding process from thermoplastic material such as polypropylene, polyethylene, polystyrene, polycarbonate, copolymers of these materials and the like, with thermoplastic elastomeric material being used for stopper 39 and selected as a material that may be successfully co-injected with the material selected for elongate body portion 29 to preferably form a single article of manufacture. It is preferred that the plunger be made in a two-shot molding process wherein the elongate body portion is formed followed by injection of a thermoplastic elastomer to form the stopper. The thermoplastic elastomeric material preferably enters the mold at or about center 89 of outside surface 37 and radiates along a radial recess 90 in outside surface 37 of end wall 35 is provided to facilitate forming of the stopper and to allow a preferably continuous relatively smooth surface at end wall 35. The at least one radial element of stopper 39 can be two or more radial elements. If two radial elements are used it is preferred that they radiate from center 89 of the outside surface in generally opposite directions.

Sleeve 68 preferably includes an outward step 67 adjacent proximal end 72. When the needle retracting process is initiated by the user's application of sufficient distal force to plunger 28, best seen in FIGS. 11-12A, outward step 67 serves as a receptacle for cut portion 47 of flange 48, when sharpened edge 74 cuts through flange 48. As further distal force is applied to plunger 28 by the user, cutting edge 74 cuts through distal wall 35 of plunger 28 including portions of stopper 39 to expose cavity 36 by cutting portion 33 from distal end 32. Once cavity 36 is exposed, spring 66 urges sleeve 68, with cut portions 33 and 47 into cavity 36 thereby withdrawing needle 12 to a position, best seen in FIGS. 13 and 13A, where sharp distal end 62 is within syringe 10 and substantially protected from inadvertent contact.

In a retracting needle syringe, such as the retracting needle syringe described herein, where a proximally facing sharp element is forced to cut in a proximal direction through portions of a stopper and a plunger rod it is important to minimize the thickness of the distal end wall of the plunger to avoid requiring more than acceptable force to activate the retraction of the needle. However, if the end wall is too thin it will have poor structural integrity and flex into shapes that frustrate the retracting of the needle into the plunger cavity. Accordingly, a balance must be reached between an end wall that has structural integrity to withstand the forces of cutting and an end wall that is not over designed and requires the user to provide more than the desired amount of force to activate the needle retracting mechanism. This problem is magnified if the plunger is integrally formed by a co-injection process having a rigid body portion and an elastomeric stopper including one or more radial projections from the center of the surface of the end wall of the plunger.

It has been found that variously sized chamfers can be utilized to provide the support necessary to prevent collapse or distortion of end wall 35 during the cutting process while avoiding the need to apply excessive force to the plunger. A chamfer under the radial element helps prevent stretching during cutting. The stretching of the stopper during cutting tends to leave a flap of the thermoplastic elastomeric material of the stopper which could interfere with the retraction of the needle assembly into the plunger.

Figure 9:
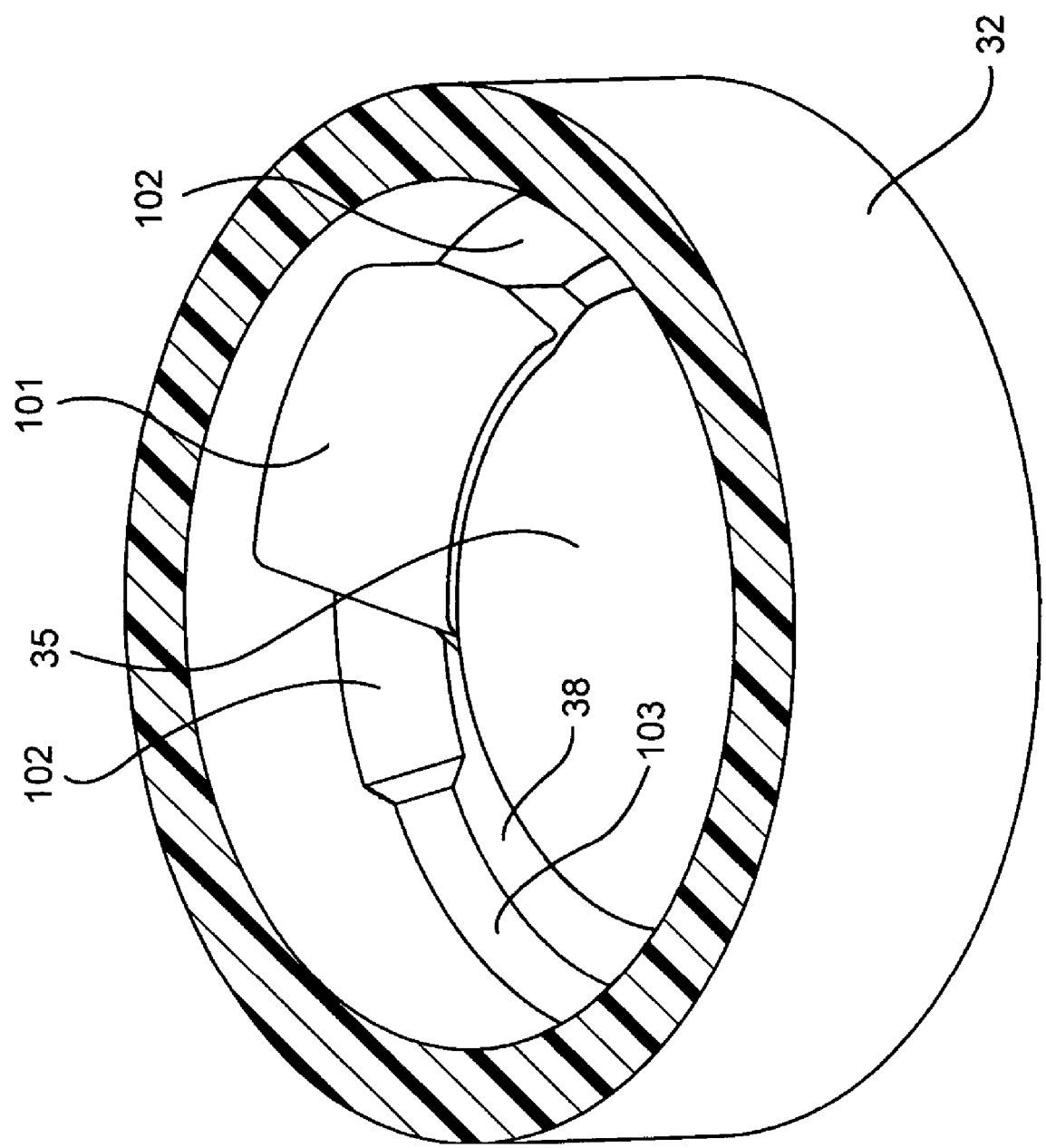
FIG. 9 is a perspective view of the inside of the distal end of the plunger of FIG. 4 illustrating the chamfer arrangement.

In one embodiment of the invention illustrated in FIGS. 1-13A, distal end 32 of elongate body portion 29 includes at least one primary chamfer 101 in cavity 36 at the intersection of inside surface 38 of the distal wall and side wall 31. The primary chamfer is positioned under radial element 88 of the stopper for supporting the distal wall and the radial element when the hollow sleeve cuts through the end wall as illustrated in FIG. 12A. A secondary chamfer 102 is positioned on each side of primary chamfer 101. The secondary chamfers are smaller than the primary chamfer for supporting the distal wall while it is being cut while providing less resistance to the action of the sharp edge of sleeve 68. As best illustrated in FIG. 9, also, in this preferred embodiment a tertiary chamfer 103 is positioned adjacent to each secondary chamfer and is smaller than the secondary chamfer for the same reasons that the secondary chamfer is smaller than the primary chamfer. In the preferred embodiment, it has been determined that best results were achieved using primary, secondary and tertiary chamfers being sized to approach a minimum cutting force while still maintaining integrity of the distal end of the plunger during the cutting procedure. As seen in side elevation cross-sectional view such as FIG. 7, the primary chamfer has a generally planar outside surface 104. The primary chamfer desirably extends for about the same number of degrees along intersection of the inside surface of the distal wall and the side wall of the elongate body portion as a width X of the radial element adjacent to the primary chamfer, as measured from longitudinal axis 41. It is desirable for the secondary chamfers to extend along the intersection of the inner surface of the distal wall and the side wall for a distance of at least one-half the distance the primary chamfer extends along the intersection. In this preferred embodiment, the secondary chamfer is at an angle of between 40 and 50° as measured from the longitudinal axis. It is also desirable that the secondary chamfers are no more than 60 percent as high as the primary chamfer. As illustrated in FIG. 7, in this preferred embodiment, primary chamfer is at an angle B between 40° and 50° measured from the longitudinal axis. Primary chamfer 101 is also preferably between 0.33 mm (0.015 inch) and 0.64 mm (0.025 inch) high as measured from inside surface 38 of the distal wall. The syringe of the preferred embodiment is intended to deliver approximately 1 ml of liquid, and in this size syringe, circular body portion of the plunger has an inside diameter at its distal end of about 2.9 to 3.4 mm (0.115 to 0.135 inch). It can be appreciated that the size, angle, shape and circumferential length of the primary and secondary chamfers can vary greatly depending on the size of the syringe, the configuration of the stopper, the size and shape of the cutting element and the materials used for the body portion of the plunger and stopper. The faces of the chamfers as shown in cross-sectional views may be planer, concave, convex or combinations thereof. The straight-sided chamfers illustrated herein are merely representative of these many possibilities. Also, acceptable forces for cutting through the end wall will affect the size and shape of the primary and secondary chamfers. In the present embodiment the stored energy in elongate spring 66 helps the sharp cutting edge of sleeve 68 to cut through the stopper and distal wall of the plunger body portion. Other designs may not have a spring and require all of the forces for activation to be provided by the user applying distally directed force to the plunger with respect to the barrel.

Figure 15:
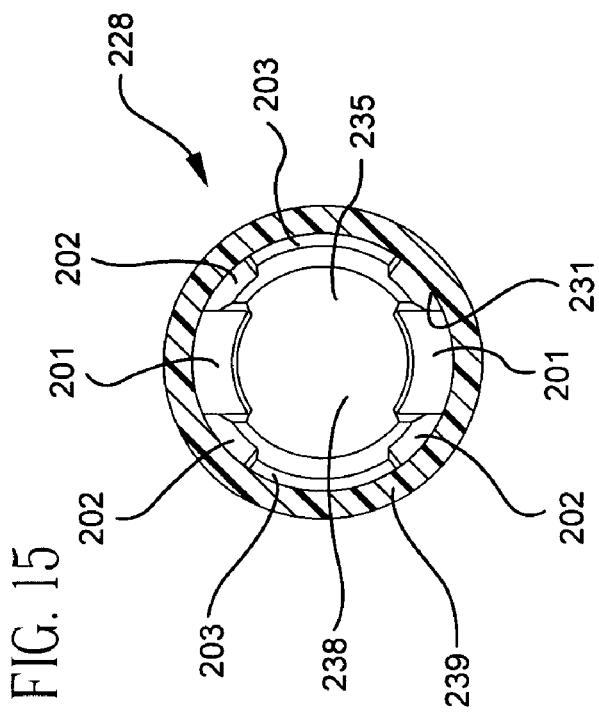
FIG. 15 is a side elevation cross-sectional view of the distal end of the interior plunger of FIG. 14.
Figure 14:
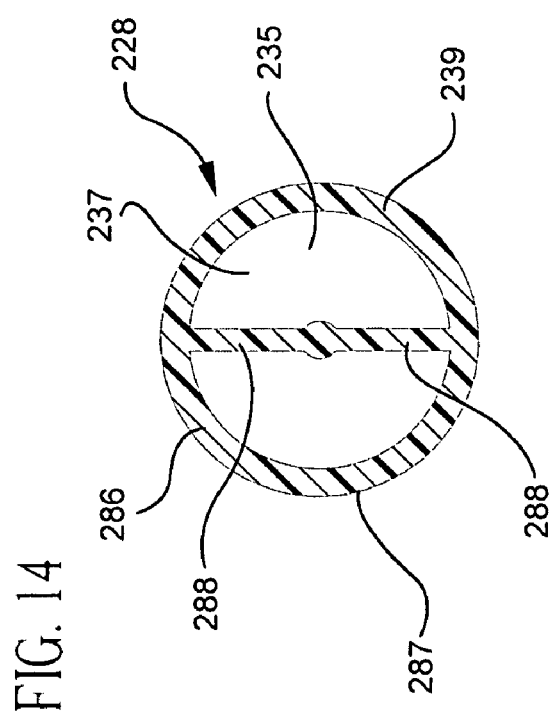
FIG. 14 is a side elevation view of the distal end of another embodiment of the plunger of the present invention.

It is also within the purview of the present invention to include a plunger having a stopper with more than one radial element and more than one set of primary and secondary chamfers. Such an alternative embodiment is illustrated in FIGS. 14 and 15 wherein plunger 228 includes an elongate body portion having a side wall 231 and a closed distal end including distal wall 235. Distal wall 235 includes an inside surface 238 and an outside surface 237. Stopper 239 at the distal end of the plunger includes a peripheral portion 286 having an outside surface 287 forming a seal with the inside surface of the barrel. Stopper 239 includes two radial elements 288 extending from about a center of outside surface 237 of the distal wall to peripheral portion 286. The interior distal end of the plunger elongate body portion includes two primary chamfers 201 in the cavity at the intersection of inside surface 238 of distal wall 235 and side wall 231. The primary chamfers are positioned under each of the radial elements of the stopper for supporting the distal wall and the radial elements when a cutting element cuts through the end wall. Secondary chamfers 202 are positioned on each side of primary chamfers 201 so that each secondary chamfer is smaller than its adjacent primary chamfer. Also, the secondary chamfers are joined by tertiary chamfers 203 which are smaller than their adjacent secondary chamfers.

Figure 16:
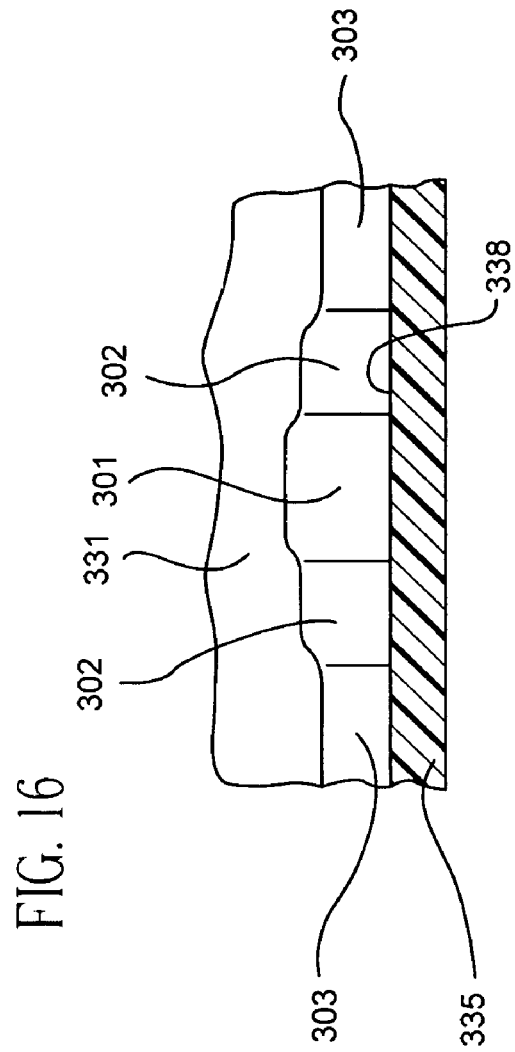
FIG. 16 is a partial side elevation cross-sectional view of the distal end of the plunger rod of another embodiment of the present invention.

Although the primary, secondary and tertiary chamfers illustrated are separate, preferably connected, and distinct elements, it should be understood that the chamfers may gently blend into each other along a continuously curvilinear line rather than the abrupt steps shown. FIG. 16 illustrates such an arrangement wherein primary chamfer 301, secondary chamfers 302 and tertiary chamfers 303 are positioned at the intersection of side wall 331 and inside surface 338 of distal wall 335. Here the primary, secondary and tertiary chamfers are blended relatively smoothly into each other and although performing the same function as the chamfers in the embodiment of FIGS. 1-13A, the chamfers of FIG. 16 have a less abrupt interface with each other and transition gradually from one to another.

Sleeve 68 is preferably formed from a metallic material such as carbon steel, stainless steel and the like. Preferably, sleeve 68 is formed by deep drawing of stainless steel and than subjected to a secondary process such as grinding, honing, polishing, electrochemical processing or combinations of these processes to produce sharp cutting edge 74 at proximal end 72 of the sleeve.

Referring to FIGS. 3 and 10-11A, inside surface 26 of hollow bore 24 preferably includes a protuberance 76 thereon for interacting with a conjugate depression 78 on flange 48 to form engagement 50 with protuberance 76. Engagement 50 serves to hold hub 42 in position in the barrel so that needle 12 projects outwardly with spring 66 in compression between flange 48 and shoulder 22 of the receiver.

Returning to FIGS. 3 and 10-13, proximal end 16 of barrel 14 further includes a finger grip 80 to facilitate a user's grip of the syringe. Additionally, elongate plug 34 is preferably retained in open proximal end of plunger 28 by an interference fit. A finger press 82 is disposed at proximal end 30 of plunger 28 to facilitate the user's movement of plunger 28 to draw and expel fluid from chamber 40 and to apply additional force to the plunger to initiate the retraction of needle 12. Finger grip 80 also includes a collar 84. It should be noted that the purpose of elongate plug 34 is to optimize the interior space of the plunger for receiving the retracting needle. There are many ways to achieve the function of elongate plug 34 and finger press 82 including having an integral elongate plug and finger press connected to the open proximal end of the plunger. The plug may be joined to the plunger through a press-fit, snap-fit, threaded arrangement, ultrasonic welding, adhesive and the like. All of these various combinations are within the purview of the present invention and the structure illustrated is merely representative of these many possibilities.

Syringe assembly 10 provides users with a selectively retractable needle syringe that is substantially usable in most normal use techniques. The syringe assembly is also compatible with many current assembly practices and machines, thus is well suited for the high speed, high volume manufacture. Additionally, since the retraction mechanism is both simple and positive. Syringe assembly 10 may readily be manufactured in small sizes such as a one milliliter capacity with an inside bore diameter of about one quarter inch. The syringe assembly provides users of conventional small capacity syringes with a selectively retractable alternate that functions similarly to standard, non-retracting needle syringes during filling and injection, thus addressing a need in the medication delivery industry. The plunger of the present invention improves the functionality of the syringe assembly by providing a structure which helps to improve the stability of the distal end of the plunger and the quality and consistency of the cut during the cutting step of needle retraction, while minimizing the cutting forces required.

The invention claimed is:

1. A plunger for an operable retracting needle syringe including a syringe barrel having an inside surface defining a chamber, an open proximal end, a distal end including a needle assembly having a hub connected to said distal end of said barrel and a needle having a sharp distal end, a proximal end connected to said hub and a lumen therethrough in fluid communication with said chamber, said hub further including a biased spring operatively connected to a hollow cutting sleeve having a proximally facing sharp edge capable of cutting through said hub and said plunger wherein said plunger comprises:

a hollow elongate body portion having a proximal end, a closed distal end and a side wall therebetween defining a cavity therein and including a longitudinal axis, said distal end including an end wall having an outside surface and an inside surface;

a stopper at said distal end of said plunger including a peripheral portion having an outside surface for forming a seal with said inside surface of said barrel, said stopper having at least one radial element extending from about a center of said outside surface of said end wall to said peripheral portion;

said distal end of said body portion including at least one primary chamfer in said cavity at an intersection of said inside surface of said end wall and said side wall, said primary chamfer supporting said end wall and said at least one radial element when said hollow sleeve cuts through said end wall, and a secondary chamfer on each side of said at least one primary chamfer, each of said secondary chamfers being smaller than said primary chamfer.

2. The plunger of claim 1 wherein said at least one radial element of said stopper includes two radial elements and said at least one primary chamfer includes two primary chamfers.

3. The plunger of claim 2 wherein said two radial elements radiate in opposed directions.

4. The plunger of claim 1 further including a tertiary chamfer adjacent to each secondary chamfer, said tertiary chamfers being smaller than said secondary chamfers.

5. The plunger of claim 4 wherein said secondary chamfers and said tertiary chamfers are blended together in a relatively smooth transition.

6. The plunger of claim 1 wherein said at least one primary chamfer is between 0.38 mm (0.015 inch) and 0.64 mm (0.025 inch) high as measured from said inside surface.

7. The plunger of claim 6 wherein said secondary chamfers are no more than 60% as high as said primary chamfer.

8. The plunger of claim 1 further including a centrally located distally directed projection for entering a recess in a proximal end of said hub for reducing the amount of liquid in said barrel after injection.

9. The plunger of claim 8 wherein said distally directed projection of said stopper is frusto-conically shaped.

10. The plunger of claim 1 wherein said at least one primary chamfer and said secondary chamfers are blended together in a relatively smooth transition.

11. The plunger of claim 1 wherein said body portion is circularly shaped having an inside diameter at said distal end of 2.9 to 3.4 mm (0.115 to 0.135 inch).

12. The plunger of claim 1 wherein said at least one primary chamfer has a generally planer outside surface.

13. The plunger of claim 1 wherein said at least one primary chamfer has a generally concave outside surface.

14. The plunger of claim 1 wherein said at least one primary chamfer extends for about the same number of degrees along said intersection as a width of said radial element adjacent to said primary chamfer, as measured from said longitudinal axis.

15. The plunger of claim 1 wherein said primary chamfer is at an angle of between 40° and 50° measured from said longitudinal axis.

16. The plunger of claim 1 wherein each of said secondary chamfers extends along an intersection of said inner surface and said side wall for a distance of at least one-half the distance said primary chamfer extends along said intersection.

17. The plunger of claim 1 wherein said secondary chamfer is at an angle of between 40° and 50° measured from said longitudinal axis.

18. The plunger of claim 1 wherein said elongate body portion is made of thermoplastic material.

19. The plunger of claim 1 wherein said stopper is made of a thermoplastic elastomer material.

20. A plunger for an operable retracting needle syringe including a syringe barrel having an inside surface defining a chamber, an open proximal end, a distal end including a needle assembly having a hub connected to said distal end of said barrel and a needle having a sharp distal end, a proximal end connected to said hub and a lumen therethrough in fluid communication with said chamber, said hub further including a biased spring operatively connected to a hollow cutting sleeve having a proximally facing sharp edge capable of cutting through said hub and said plunger wherein said plunger comprises:

a hollow elongate thermoplastic body portion having a proximal end, a closed distal end and a side wall therebetween defining a cavity therein and including a longitudinal axis, said distal end including an end wall having an outside surface and an inside surface;

a thermoplastic elastomer stopper at said distal end of said plunger including a peripheral portion having an outside surface for forming a seal with said inside surface of said barrel, said stopper having at least one radial element extending from about a center of said outside surface of said end wall to said peripheral portion;

said distal end of said body portion including at least one primary chamfer in said cavity at an intersection of said inside surface of said end wall and said side wall, said primary chamfer supporting said end wall and said at least one radial element when said hollow sleeve cuts through said end wall, said at least one primary chamfer extending about the same number of degrees along said intersection as a width of said radial element adjacent to said primary chamfer, as measured from said longitudinal axis, and a secondary chamfer on each side of said at least one primary chamfer, each of said secondary chamfers being smaller than said primary chamfer and extending along said intersection.

21. The plunger of claim 20 wherein said primary chamfer is at an angle of between 40° and 50° measured from said longitudinal axis.

22. The plunger of claim 21 wherein said at least one primary chamfer is between 0.38 mm (0.015) inch) and 0.64 mm (0.025 inch) high as measured from said inside surface.

23. The plunger of claim 20 wherein said body portion is circularly shaped having an inside diameter at said distal end of 2.9 to 3.4 mm (0.115 to 0.135 inch).

24. The plunger of claim 20 wherein said at least one primary chamfer has a generally planer outside surface.

25. The plunger of claim 20 wherein said at least one primary chamfer has a generally concave outside surface.

* * * * *